United States Patent [19]

Pozzi et al.

[11] Patent Number: 5,176,639
[45] Date of Patent: Jan. 5, 1993

[54] SINGLE-INJECTION SYRINGE

[75] Inventors: Didier Pozzi, 8, rue Paul-Houette; Jean-Pierre Pozzi, 6, allée des Tilleuls, both of F-92190 Meudon, France

[73] Assignees: Jean-Edouard Clotteau, Paris; Didier Pozzi; Jean-Pierre Pozzi, both of Meudon, all of France

[21] Appl. No.: 477,804

[22] PCT Filed: Jun. 1, 1989

[86] PCT No.: PCT/FR89/00270
§ 371 Date: Feb. 2, 1990
§ 102(e) Date: Feb. 2, 1990

[87] PCT Pub. No.: WO89/11886
PCT Pub. Date: Dec. 14, 1989

[30] Foreign Application Priority Data

Jun. 3, 1988 [FR] France .................. 88 07412
Dec. 30, 1988 [FR] France .................. 88 17474

[51] Int. Cl.⁵ ............................................ A61M 5/315
[52] U.S. Cl. ................................... 604/110; 604/228; 604/236
[58] Field of Search .......... 604/90, 110, 187, 203, 604/205, 226, 228, 229, 236-238, 218

[56] References Cited

U.S. PATENT DOCUMENTS

| 4,059,109 | 11/1977 | Tischlinger | 604/90 |
| 4,233,975 | 11/1980 | Yerman | 604/110 |
| 4,687,487 | 8/1987 | Cygielski | 604/110 |
| 4,863,427 | 10/1989 | Cocchi | 604/110 |
| 4,880,410 | 11/1989 | Rossmark | 604/110 |
| 4,973,308 | 11/1990 | Borras et al. | 604/228 X |

FOREIGN PATENT DOCUMENTS

| 0229017 | 7/1987 | European Pat. Off. | |
| 0210386 | 6/1974 | Fed. Rep. of Germany | 604/110 |
| 2205343 | 5/1974 | France | |
| 2298340 | 8/1976 | France | 604/110 |
| 2606643 | 5/1988 | France | 604/110 |
| 2450263 | 4/1976 | German Democratic Rep. | 604/228 |

Primary Examiner—John D. Yasko
Assistant Examiner—Anthony Gutowski
Attorney, Agent, or Firm—Armstrong & Kubovcik

[57] ABSTRACT

Inside a syringe (1) slides a plunger (2) which bears a joint (4) sliding sealingly over the internal wall of the syringe. The flexible membrane (6) of the joint (4) fixed to the end of the plunger (2) bears a closing component (25, 27) which follows the movement of deformation or displacement of the membrane through the effect of the pressure built up during the injection stage, but which is retained by immobilizing strips (17) in a position in which it opens the orifice, breaking the seal between the top and the bottom of the joint, as soon as the membrane returns to its initial position.

5 Claims, 5 Drawing Sheets

SINGLE-INJECTION SYRINGE

FIELD OF THE INVENTION

The present invention relates to a disposable syringe, that is one that can be used only once, and relates more precisely to a device that renders the sealing joint inoperative after a first injection.

BACKGROUND OF THE INVENTION

In the field of therapeutics, the use of syringes for injecting fluids into tissues or natural cavities in the body is extremely widespread. A syringe is known to be composed essentially of a cylindrical barrel in which a plunger slides, a body whose base bears a nozzle of a suitable shape to which can be fitted a hollow needle, for example a needle made of steel or nickel, the barrel thus forming a reservoir for the fluid to be injected. The structure or composition of the plunger can vary according to the model. It is, in any case, provided at one of its ends with a joint to ensure sealing with the barrel of the syringe and, at its other end, which is always external to the barrel of the syringe, a plunger head to facilitate its handling. This classical syringe makes it possible to perform in the habitual manner the operations required for an injection as commonly practised, that is in the first place, detaching the joint at the bottom of the syringe and then, by applying traction to the plunger to extract it from the barrel of the syringe, drawing in a certain quantity of fluid. Then, with the syringe in inverted position, that is with the needle pointing upwards, a slight pressure on the plunger causes any air remaining in the reservoir to be discharged, this operation possibly being followed by the drawing in of a complementary quantity of fluid and again the essential discharge of the air.

Before injection properly speaking, slight re-aspiration is practised after insertion for checking purposes.

There are known disposable syringes used for vaccinations which are pre-filled in the laboratory and with which it is no longer possible to draw in fluid after the injection. However, as most syringes used are not pre-filled and since it has to be possible for the to and fro movements of the plunger to be performed for the operations described above, or for manipulations in an empty condition, it is not possible to adopt this system.

SUMMARY OF THE INVENTION

One object of the present invention is thus to provide a device adaptable to any syringe, which permits the performance of all the operations necessary for a complete injection and thus including the to and fro movements of the plunger or its manipulation in an empty condition as described above, but which strictly precludes re-use for a second injection, the device rendering the sealing joint inoperative after the first injection by making use of the action of the pressure exerted by the fluid, during injection, on a flexible part of the joint to detach the joint from its driving plunger, or to destroy its function as a sealing member.

The invention thus relates to a disposable syringe comprising a cylindrical syringe barrel to the base of which can be fixed different sorts of sampling and/or injection needles, as well as a plunger sliding inside the syringe barrel and whose end bears a joint the slides sealingly over the internal wall of the syringe, a syringe in which the joint comprises at least one member capable of being deformed or displaced from its position of equilibrium through the action of the pressure exerted by the fluid contained in the syringe at the time of the injection stage, the sliding plunger being associated with the joint via components that react to the deformation or the displacement of the member and which render the joint inoperative for the purposes of refilling after the injection.

According to the special features of the invention, the joint is a hollow cylindrical component whose lower face is formed by a flexible membrane that constitutes the deformable member and which ensures sealing between the syringe barrel and the chamber inside the joint and whose annularly shaped upper portion bears against the plunger, which plunger extends, through the orifice in the annular portion of the joint, by an axial rod having a diameter less than that of the orifice and ending in a head forming a shoulder with the rod.

According to one special feature of the invention, the flexible membrane or the displaceable member has an orifice that is normally tightly closed by a closing component which follows the movement of deformation or displacement of the membrane or of the member through the effect of the pressure built up during the injection stage, but which is retained by an immobilizing device in a position in which it opens the orifice, breaking the seal between the top and bottom of the joint, as soon as the membrane or the member returns to its initial position.

DESCRIPTION OF THE DRAWINGS

Other special features and advantages of the invention will emerge as a result of reading the following description of examples of embodiments with reference to the annexed drawings, wherein.

DESCRIPTION OF THE PREFERRED EMBODIMENTS

Figure 1:
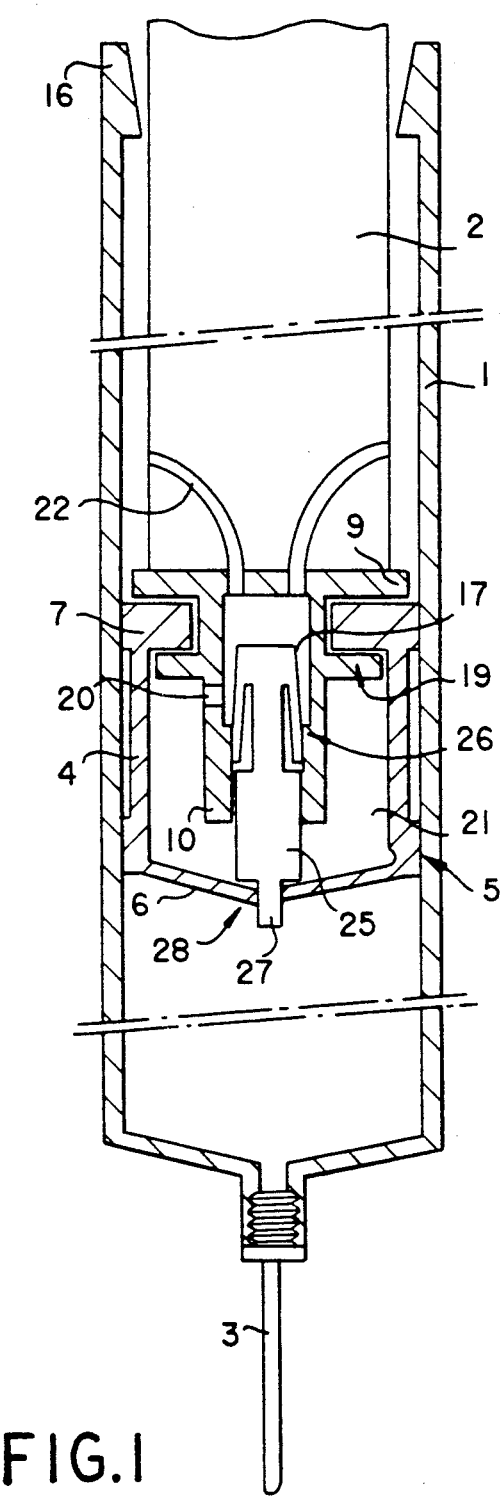
FIG. 1 is a schematic view in elevation of an equipped syringe in a rest position.

The syringe represented in FIG. 1 is composed essentially of a cylindrical syringe barrel 1 to the base of which is fixed a sampling or injection needle 3, a plunger 2 sliding inside the syringe barrel and a sealing joint 4 mounted on the end of the plunger and sliding sealingly over the internal wall of the syringe. The plunger cannot be withdrawn from the barrel of syringe 1 because of a non-return device 16 which prevents any interference with the device. The sealing joint 4 takes the form of a hollow cylindrical component whose external wall is provided with integrally moulded ribs 5, forming a seal on the internal wall of syringe barrel 1. The lower face of the joint, opposite the orifice in the syringe barrel, forms a flexible membrane 6 whose thickness is reduced in relation to the rest, a membrane which, in the position of equilibrium, is substantially horizontal and ensures sealing between the syringe barrel and a chamber 21 internal to the joint. On the other side, the upper portion 7 of the annularly shaped joint, bearing against a shoulder 9 of the plunger, is thicker and is provided with a central orifice 28. The lower face of this upper portion 7 of the joint bears against a shoulder 19 projecting from a hollow cylindrical rod 10 which prolongs the plunger 2 and extends inside the joint. Joint 4 is thus made integral with the plunger 2. Inside the hollow rod 10 is placed a closing component 25, having a generally elongated shape, and whose cross-section is cylindrical or star-shaped. This component is able to move with a slight amount of clearance inside the shaft constituted by rod 10 which further bears an internal shoulder 26 delimiting within the rod a lower shaft having a smaller cross-section than the upper shaft at the annular portion 7. The shoulder could also be a boss covering or otherwise the entire circumference of the shaft. The closing component 25 ends towards the bottom in a closing head 27 which closes a small orifice 28 provided in the membrane 6. On its upper portion, closing portion 25 carries elastic strips 17 held folded back when they are applied against the internal wall of rod 10, and which play the part of a non-return member, as we shall see later. It will be noted that rod 10 is traversed by ports 20 placing the internal chamber 21 of the joint 4 in communication with the internal shaft of the rod and, thereby, via ports 22 provided in the plunger, with the syringe above the shoulder of the plunger. The position represented in the FIG. 1 corresponds to the pre-injection stage. Head 27 of the closing component 25 sealingly closes the membrane 6, following its movement.

Figure 2:
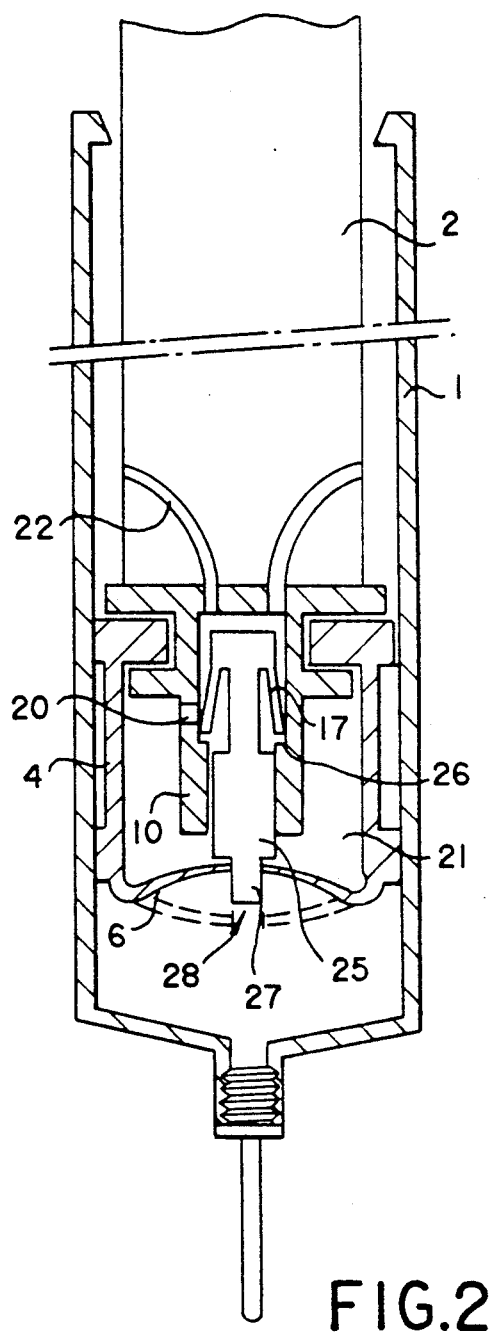
FIG. 2 shows the same syringe during an injection stage.

Directly the injection stage commences, as represented in FIG. 2. Through the effect of the pressure built up, membrane 6 is deformed from the position shown in dashed lines to the position shown in solid lines. The closing component 25 follows this movement and the elastic strips 17 then escape from the lower shaft and spread out in the upper well. They will then be immobilized by the shoulder 26, making any return of the component to its initial position impossible. This non-return function only takes effect if the pressure in the reservoir has reached a predetermined maximum value, the displacement of the closing component remaining reversible for all values lower than the said pressure. Following injection, the joint 4 remains integral with the plunger but, as the deformed portion of the membrane 6 is no longer subjected to the positive pressure, it has regained its initial shape. However, the closing head 27 remains at a distance from the membrane and orifice 28 is disengaged. Chamber 21 is connected to atmosphere by the ports 22 provided in plunger 2, and by ports 20, and also communicates with the bottom of the syringe via orifice 28. The seal is thus broken between the top and the bottom of the joint. Thus, it becomes impossible to fill the injection device by drawing in fluid or through the action of a pressurized fluid, or to perform an injection.

According to another form of embodiment, not shown, it can be contemplated that the bottom 6 remains rigid but that it is the side walls of the joint 4, below its annular portion 7, that are deformed and fold at the time of the injection stage and displace the base of the joint and the closing component upwards.

According to yet another form of embodiment, not shown, the closing portion is not fitted with non-return elastic strips 17 but is stuck in the top position against the plunger by means of an adhesive or a suitable glue located on the plunger and/or the component.

Figure 3:
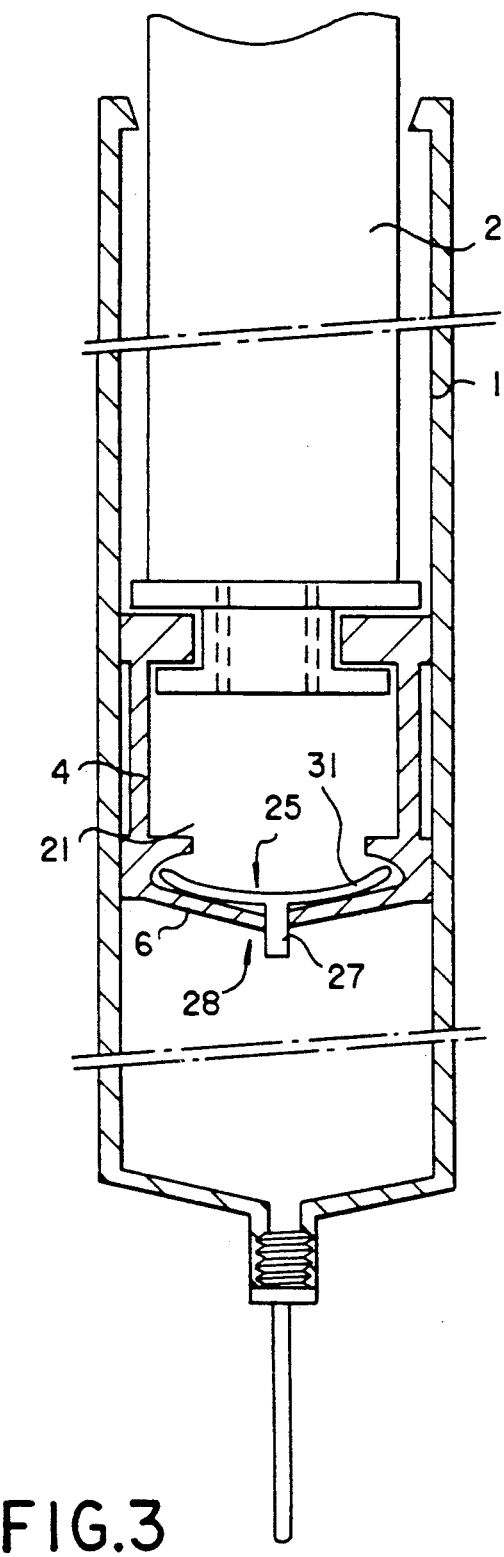
FIGS. 3 and 4 show another form of embodiment, also in two positions.
Figure 4:
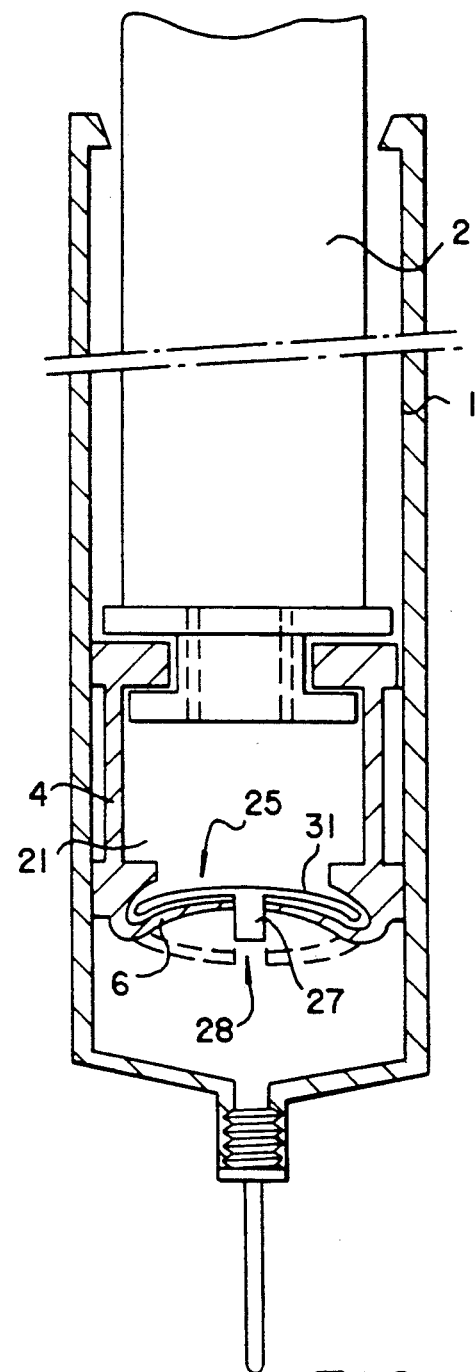

FIGS. 3 and 4 show yet another form of embodiment, again in the two habitual operating stages. This time, the closing component 25 is constituted by a dome-shaped strip 31 the concavity of which is directed downwards, in the same direction as that of the undeformed membrane 6 of the joint 4 inside which it is maintained. The dome-shaped strip 31 bears in its center a closing head 27 which also cooperates with orifice 28. In the initial stage (FIG. 3), strip 31 is in a cambered position, as shown, in which orifice 28 is closed. At the time of the injection stage illustrated in FIG. 4, the positive pressure in the syringe is sufficient for deformation of the membrane 6 to push the dome-shaped strip 31 upwards. Its concavity then changes direction and it remains in this position. When the membrane regains its initial position, at the end of injection, orifice 28 is no longer closed by closing head 27 since the strip has remained cambered in the upper position. It will be noted that the friction between the head 27 and the edges of the membrane around its orifice 28 is insufficient to return dome-shaped strip 31 from the position shown in FIG. 4 to that shown in FIG. 3 merely through the traction of membrane 6 returning to its initial position.

According to another form of embodiment, not shown, the dome-shaped strip, instead of being associated with the joint 4, could be associated with a displaceable rigid member.

In the case of the variants in FIGS. 3 and 4, operation and the result obtained are the same as in the case described with reference to FIGS. 1 and 2.

The invention has been described with reference to a joint 4 that takes the form of a hollow cylindrical component whose external wall is provided with integrally moulded ribs forming a seal on the internal wall of syringe barrel 1, and whose lower portion is a deformable membrane 6. The invention can also be considered as applying to a syringe plunger fitted with at least an added joint or profiled so as to act as a joint itself, which would be equipped with a deformable member playing the same part as that described above, or with a displaceable component instead of providing for displacement of the bottom of the joint, described earlier, through the effect of pressure.

To improve non-reutilization security yet further, it can be advantageous to provide for an area of weakness, for example at closing head 27. Any attempt to restore the closing component 25 to its initial position by traction would result in rupture between the head and the closing component.

Figure 5:
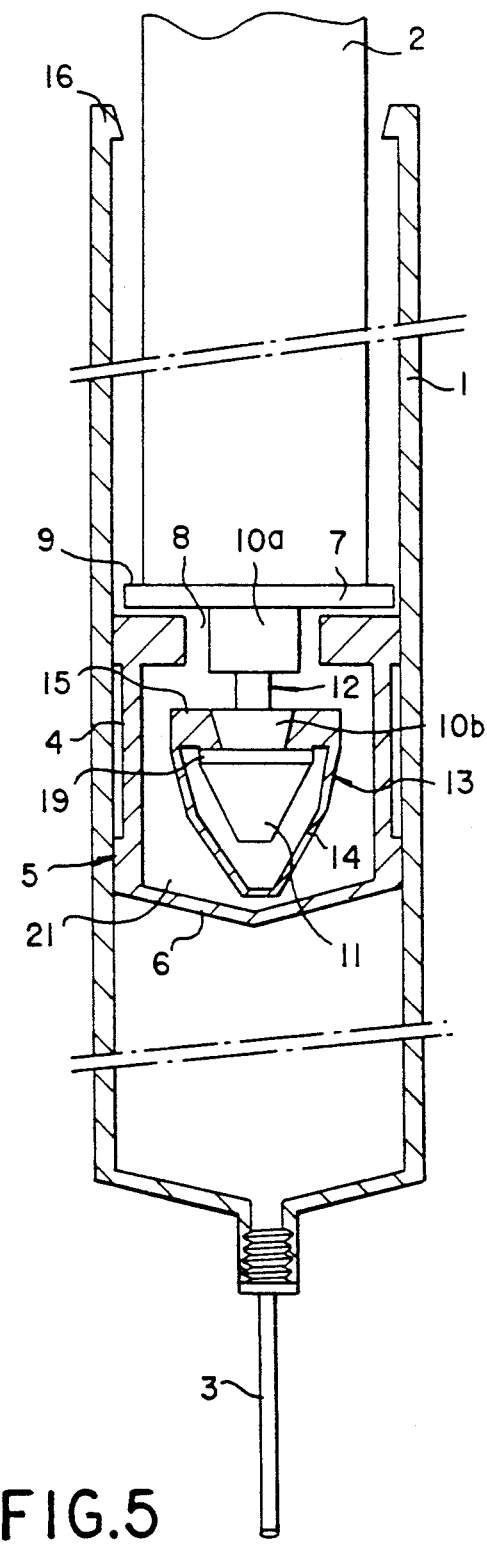
FIGS. 5 and 6 show another variant of a syringe equipped with a device for detaching the joint in a rest position and in an injection position.
Figure 6:
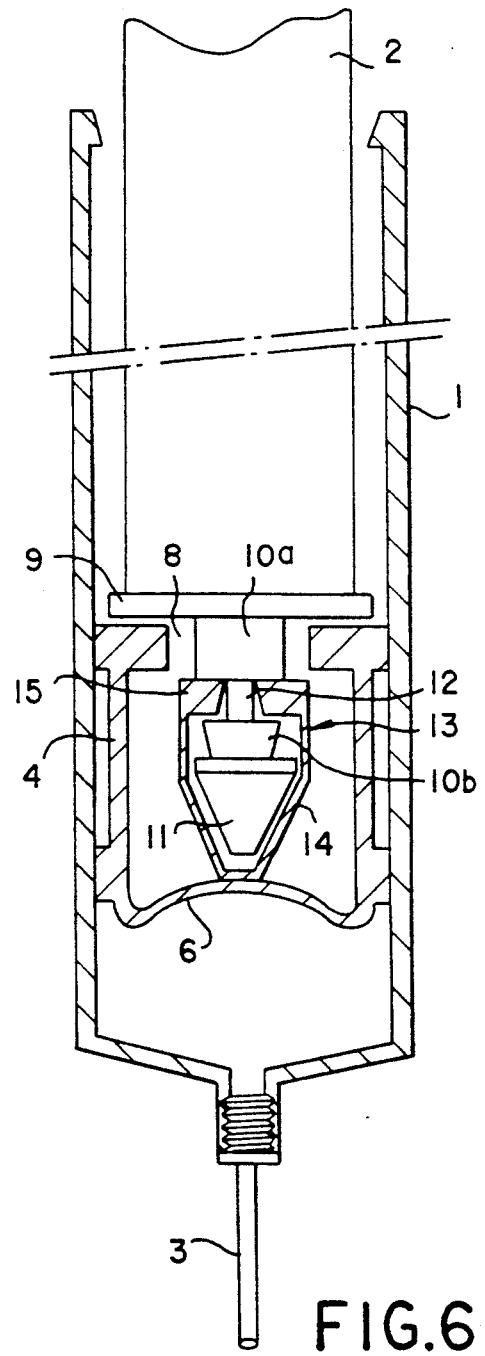

We shall now describe, with reference to FIGS. 5 and 6, another form of embodiment in which, this time, the membrane 6 of joint 4 is no longer perforated and remains tight but contains a device that detaches the joint from the plunger.

It can be see from FIG. 5, in which the same reference numbers are used for the same components as those described in connection with FIG. 1, that axial rod 10 which extends the plunger has a portion 10a with a diameter substantially less than the diameter of orifice 8, at the orifice, and that the rod ends in a conical head 11 with a larger diameter forming a shoulder 19 with the rod, a conical head whose tip is orientated towards the membrane 6 of the joint, the diameter of the shoulder remaining less than the diameter of orifice 8. Rod 10 has a neck 12 between shoulder 9 and conical head 11, the head being conical to enable the plunger to be mounted more easily on a clamp. Portion 10b of the rod between the neck and the conical portion has been bevelled to present a slightly conical profile, as seen from FIG. 5. An elastic clamp 13 formed by arms 14 which turn inwards by jaws 15 towards the center of the syringe is arranged inside joint 4 and caps conical head 11. It is shown spread in FIG. 5 and its jaws 15 whose ends have a conical profile corresponding to that of portion 10b bear against portion 10b of rod 10 and against the upper shoulder of the conical portion.

If a downward pressure is applied to plunger 2, shoulder 9 pushes against the upper face 7 of the joint. If, on the other hand, upward traction is applied to the plunger, starting from the position shown in FIG. 5, for example to ensure that fluid is drawn into the syringe, the jaws 15 of the clamp held apart by portion 10b by a distance greater than the diameter of orifice 8 abut against the annular portion 7 of the joint and enable the latter to be driven together with the plunger. The way in which the plunger and the joint are thus rendered integral permits the operations prior to injection mentioned previously.

FIG. 6 illustrates the final stage of fluid injection while the plunger 2 is descending towards the bottom of syringe 1. At that moment, the pressure of the fluid in the syringe, through the effect of the thrust of joint 4, causes deformation of the membrane 6, which bulges towards the interior of the joint 4. The membrane then bears against clamp 13, displacing it upwards until the jaws 15 escape from portion 10b of the rod and, as a result of the elasticity of arms 14, close up in groove 12. The spread of the clamp is then reduced to a size that is less than that of orifice 8 and it will then be appreciated that, following injection, if it is attempted to draw the plunger out of the syringe, the clamp will pass through orifice 8 and the joint will remain at the bottom of the syringe. It will be noted that, even if this detachment from the joint through withdrawal of the clamp has occurred at the start of the depression stroke of the plunger, injection will not be adversely affected thereby and will be able to continue normally thanks to the thrust of shoulder 9 against the joint. At the end of the stroke, conical head 11 of plunger 2, through its action on membrane 6, will press the latter against the bottom of the syringe, enabling all the fluid to be injected. The deformation of the joint in this final stage is of no importance since, in any case, the clamp will no longer be able to cooperate with annular portion 7 of the joint, which will remain at the bottom.

If, for any reason, the jaws of clamp 13 should fail to escape from portion 10b of the rod, as a result of the pressure, detachment would nonetheless occur when the clamp came into abutment through the membrane with the bottom of the syringe, at the end of the plunger travel stroke.

The clamp which can be seen in FIGS. 5 and 6 can have a profile that differs from that shown and, in particular, a lower face, from which extend arms 14, that is substantially larger, to avoid sliding on membrane 6 and to cooperate more easily therewith at the end of injection.

There will now be described yet another form of embodiment in which membrane 6 is impervious, as in the above cases, and not provided with an orifice, but in which, on the other hand, it can be perforated.

This variant is described with reference to FIGS. 7 and 8, which show that conical head 11, still integral with plunger 2 via rod 10, and housed inside joint 4, is larger in size. Its shoulder 19 in relation to the rod abuts against the annular lower portion 7 of joint 4, capping orifice 8. This annular portion 7 of the joint is thus pinched between shoulder 9 and shoulder 19; the joint and the plunger are thus rendered inseparable. As in the cases illustrated in FIGS. 5 to 6; conical head 11 is traversed by ports 20 placing the internal chamber 21 of joint 4 in communication with orifice 8. Other ports 22 are provided in the plunger itself so that there is free communication of air between chamber 21 and the syringe, above shoulder 9 of the plunger. In addition, conical head 11 is provided at its end with a point 23 orientated towards membrane 6, a point that could also be replaced by a cutting part of any shape.

Figure 7:
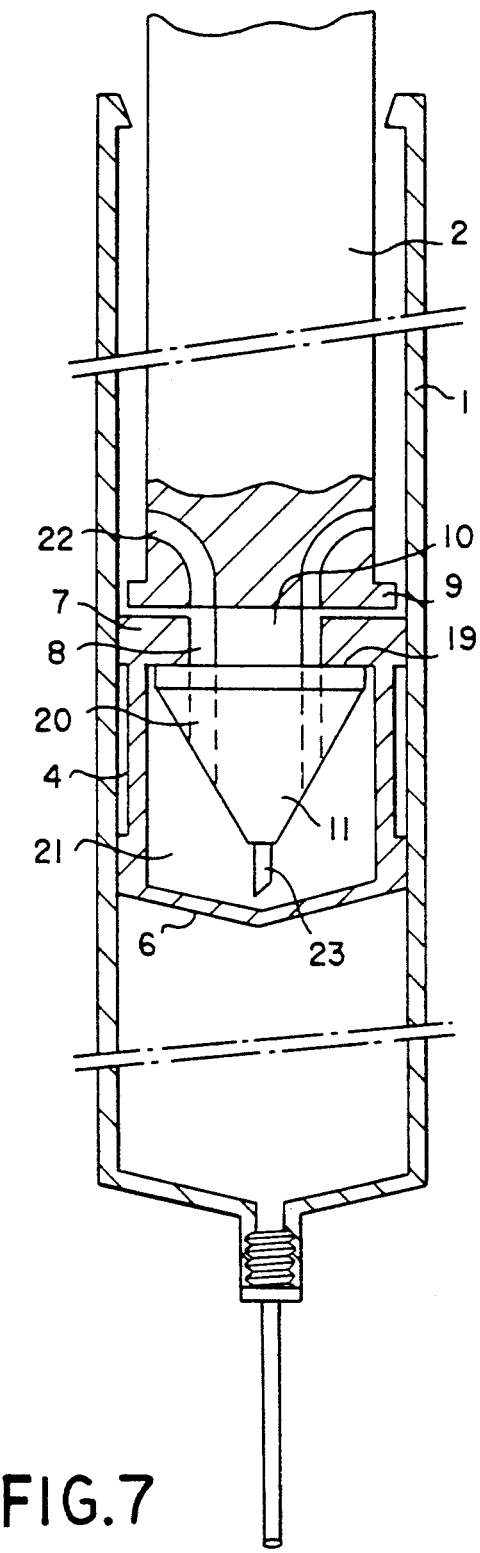
FIGS. 7 and 8 show a schematic elevation view of a syringe equipped with a device for perforating the joint, in a rest position and in an injection position.
Figure 8:
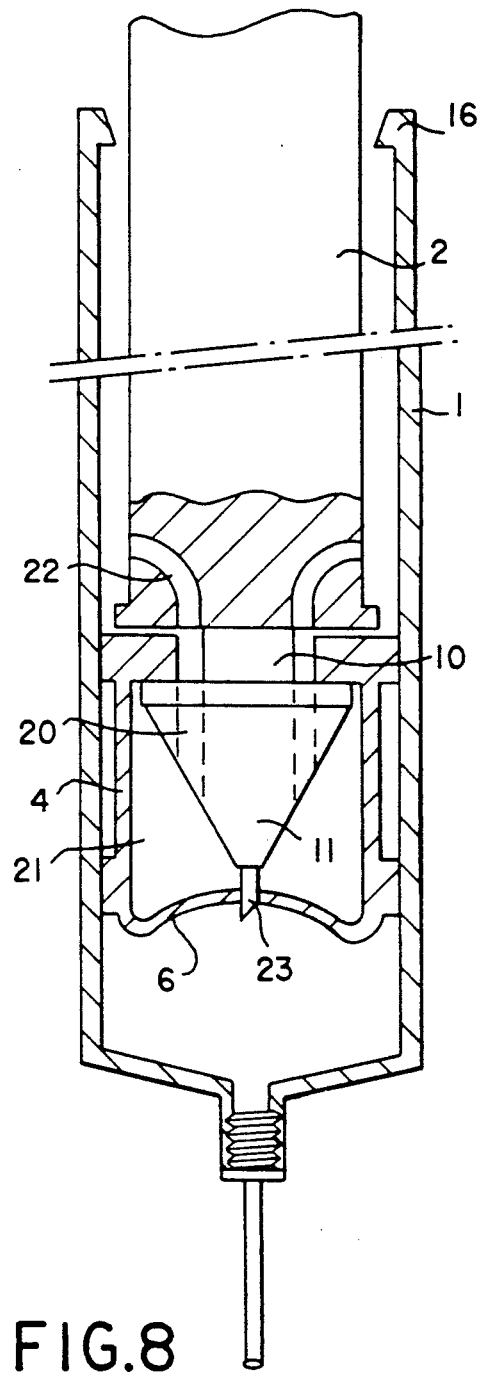

In the position represented in FIG. 7, which corresponds to a stage in operations that is preliminary to injection properly speaking, membrane 6 occupies a position of equilibrium that holds it away from point 23. Once the injection stage takes place and the pressure of the fluid becomes sufficient to deform membrane 6, the latter is pressed hard against point 23 and is perforated (FIG. 8). Nonetheless, injection can be pursued normally as the point blocks the perforation and prevents the fluid from entering chamber 21. At the end of injection, joint 4 remains integral with the plunger, as seen earlier, but if it is attempted to draw in fluid again with a view to another injection, the perforation of membrane 6 will make this operation impossible. Air will, in fact, have been able to pass through ports 20, 22 and the perforation, and to penetrate to the bottom of the syringe, definitively preventing the application of any negative air pressure and any possibility of drawing in fluid. Non-return device 16 or any other system obstructing the syringe on the upper portion but allowing the plunger to slide also prevents any interference with the syringe in all the cases described.

Figure 9:
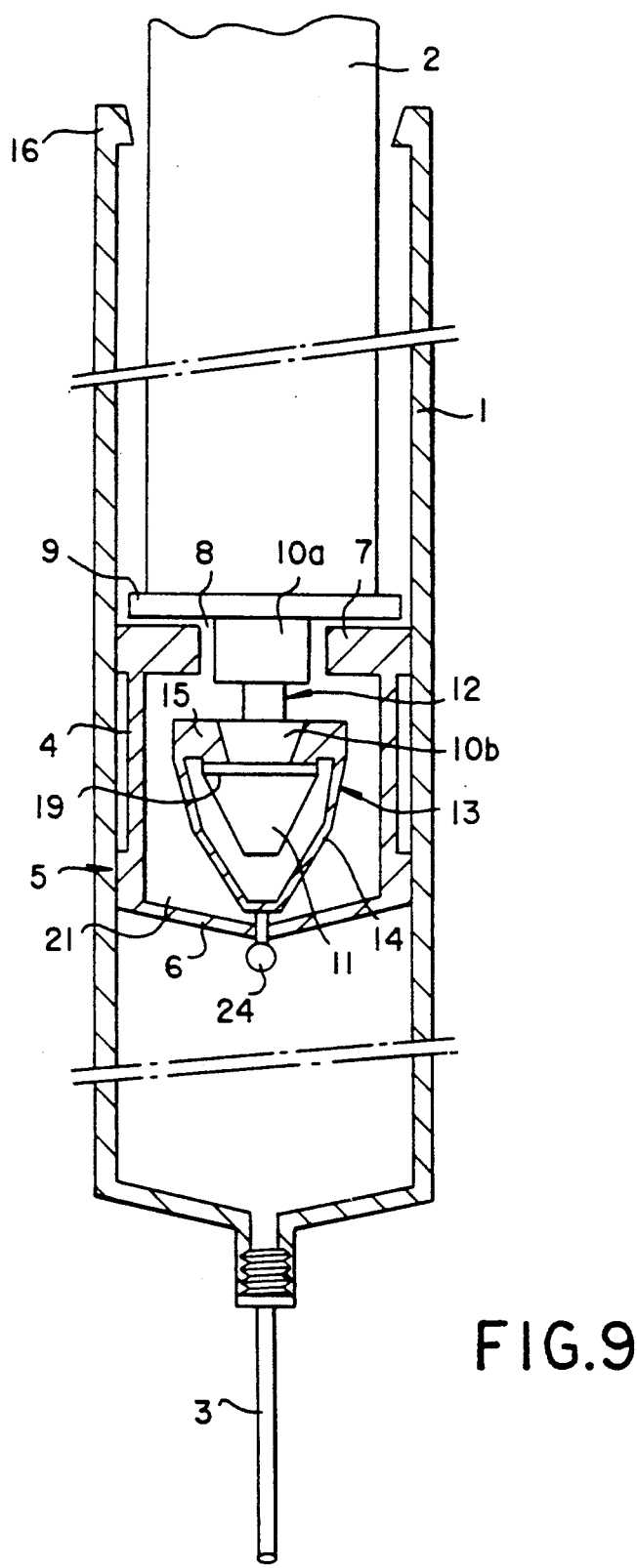
FIG. 9 shows an alternative form of embodiment.

According to yet another form of embodiment, illustrated in FIG. 9, clamp 13, used in accordance with the third form of embodiment in conformity with FIGS. 5 and 6, has on its lower portion a protuberance 24 which can have the shape of a tip with a rounded end. When the joint is mounted, steps are taken to ensure that the protuberance 24 is on the other side of membrane 6 in relation to the clamp, the tip of the protuberance passing through a central hole provided on the membrane.

The clamp and the membrane are thus rendered integral.

Operation is identical with that described in connection with the form of embodiment of FIGS. 5 and 6, that is the bulging of membrane 6 at the time of injection pushes upwards clamp 13 the jaws of which could close up in groove 12. If a user attempts to extract plunger 2, the driving of clamp 13 will draw out protuberance 24, unblocking the hole provided on the membrane, and there will remain this hole in joint 4 which will represent, in addition to the joint and the plunger being detached from one another, an additional deterioration of the joint rendering it inoperative. It will be noted that the protuberance can be withdrawn through the membrane owing to forces of friction of the joint in the syringe barrel being greater than the force of retention of the protuberance by the hole in the membrane. We thus come back to the cases illustrated in FIGS. 1 to 4.

A supplementary advantage of this variant is that the clamp is thus perfectly positioned in relation to the joint.

The devices thus described can be adapted to all types of syringes. Apart from the fact that they are perfectly efficient and strictly prevent reutilization of the syringes equipped therewith, they are simple to make and thus inexpensive.

We claim:

1. A disposable syringe comprising:
   a cylindrical syringe barrel;
   means for attaching a needle at one end of said syringe barrel;
   a plunger mounted for movement toward and away from said one end of said syringe barrel;
   a hollow member mounted at one end of said plunger for sliding movement internally of said syringe barrel, said hollow member including a deformable element disposed between said plunger and said one end of said syringe barrel, said deformable element is disposed in one position and capable of displacement to a second position upon movement of said plunger toward said one end of said syringe barrel, said deformable element having an orifice;
   at least one external rib on said hollow member providing a seal between said hollow member and an internal surface of said syringe barrel; and
   closing means located between said plunger and said deformable element of said hollow member, said closing means closing said orifice when said deformable element is initially in said one position, and movable to a second position in response to movement of said deformable element to said second position to prevent a second aspiration of a liquid following a first aspiration of liquid by movement of said plunger away from said one end of said syringe barrel whereby said closing means disengages from and opens said orifice upon corresponding displacement of said deformable element from said second position.

2. A disposable syringe comprising:
   a cylindrical syringe barrel;
   means for attaching a needle at one end of said syringe barrel;
   a plunger mounted for movement toward and away from said one end of said syringe barrel;
   a hollow cylindrical member mounted at one end of said plunger for sliding movement internally of said syringe barrel, said hollow member including an annular shaped upper portion which bears against said plunger and a flexible membrane forming a surface facing said one end of said syringe barrel and disposed between said plunger and said one end of said syringe barrel, said flexible membrane is disposed in one position and capable of displacement to a second position upon movement of said plunger toward said one end of said syringe barrel;
   an orifice in said flexible membrane;
   at least one external rib on said hollow member providing a seal between said hollow member and an internal surface of said syringe barrel; and
   closing means located between said plunger and said flexible membrane of said hollow member, said closing means closing said orifice when said flexible membrane is initially in said one position, and movable to a second position in response to movement of said flexible membrane to said second position to prevent a second aspiration of a liquid following a first aspiration of liquid by movement of said plunger away from said one end of said syringe barrel, whereby said closing means opens said orifice upon corresponding displacement of said flexible membrane from said second position.

3. A disposable syringe according to claim 2, wherein the closing means follows the movement of said flexible membrane through pressure built up at the time of injection, and said closing means is retained by an immobilizing means in a position in which said closing means opens the orifice, breaking a seal between a top and bottom of the hollow member, as soon as the flexible membrane returns to an initial position.

4. A disposable syringe according to claim 3, wherein the closing means is mounted inside a hollow rod bearing an internal shoulder which extends the plunger and includes a closing head at the end of said hollow rod which closes the orifice provided in the flexible membrane.

5. A disposable syringe according to claim 3, wherein the immobilizing means for immobilizing the closing means are constituted by elastic strips borne by said closing means and folded back inside a hollow rod, said elastic strips gripping an internal shoulder of the hollow rod when the closing means has been displaced by deformation of the flexible membrane.

* * * * *